(12) United States Patent
Nielsen et al.

(10) Patent No.: US 10,080,848 B2
(45) Date of Patent: Sep. 25, 2018

(54) DRUG DELIVERY DEVICE WITH MOVABLE NEEDLE MOUNT

(71) Applicant: Novo Nordisk A/S, Bagsvaerd (DK)

(72) Inventors: Christian Hoejris Nielsen, Copenhagen NV (DK); Kristoffer Aagaard Eriksen, Copenhagen NV (DK)

(73) Assignee: Novo Nordisk A/S, Bagsvaerd (DK)

( * ) Notice: Subject to any disclaimer, the term of this patent is extended or adjusted under 35 U.S.C. 154(b) by 83 days.

(21) Appl. No.: 15/035,563

(22) PCT Filed: Nov. 12, 2014

(86) PCT No.: PCT/EP2014/074336
§ 371 (c)(1),
(2) Date: May 10, 2016

(87) PCT Pub. No.: WO2015/071289
PCT Pub. Date: May 21, 2015

(65) Prior Publication Data
US 2016/0287812 A1    Oct. 6, 2016

Related U.S. Application Data

(60) Provisional application No. 61/904,277, filed on Nov. 14, 2013.

(30) Foreign Application Priority Data

Nov. 12, 2013    (EP) .................................... 13192550

(51) Int. Cl.
*A61M 5/24* (2006.01)
*A61M 5/28* (2006.01)
(Continued)

(52) U.S. Cl.
CPC ................ *A61M 5/36* (2013.01); *A61M 5/20* (2013.01); *A61M 5/2033* (2013.01);
(Continued)

(58) Field of Classification Search
CPC .............. A61M 5/20; A61M 2005/208; A61M 2005/2474; A61M 2005/3126;
(Continued)

(56) References Cited

U.S. PATENT DOCUMENTS

| 3,115,133 A | 12/1963 | Morando | |
|---|---|---|---|
| 2003/0036725 A1* | 2/2003 | Lavi | A61M 5/2066 604/91 |
| 2005/0090781 A1 | 4/2005 | Baba et al. | |

FOREIGN PATENT DOCUMENTS

| WO | 9411039 A1 | 5/1994 |
|---|---|---|
| WO | 0224259 A2 | 3/2002 |
| WO | 2005/077441 A2 | 8/2005 |
| WO | 2011/051366 A2 | 5/2011 |

(Continued)

*Primary Examiner* — Jason Flick
(74) *Attorney, Agent, or Firm* — Wesley Nicolas

(57) ABSTRACT

The present invention provides a drug delivery device (1) comprising a dose delivery mechanism and a blocking structure (80, 180) for preventing inadvertent activation of the dose delivery mechanism. The blocking structure (80, 180) enables and disables the dose delivery mechanism dependent on the position of a needle holder (30, 130) relative to a drug cartridge holder (20, 120).

25 Claims, 5 Drawing Sheets

(51) Int. Cl.
   *A61M 5/36*    (2006.01)
   *A61M 5/20*    (2006.01)
   *A61M 5/31*    (2006.01)
   *A61M 5/315*   (2006.01)
   *A61M 5/30*    (2006.01)

(52) U.S. Cl.
   CPC ............ *A61M 5/2466* (2013.01); *A61M 5/30* (2013.01); *A61M 5/3146* (2013.01); *A61M 5/31536* (2013.01); *A61M 5/31553* (2013.01); *A61M 5/31568* (2013.01); *A61M 5/31573* (2013.01); *A61M 5/31583* (2013.01); *A61M 5/31585* (2013.01); *A61M 2005/208* (2013.01); *A61M 2005/2474* (2013.01); *A61M 2005/3126* (2013.01); *A61M 2205/502* (2013.01)

(58) Field of Classification Search
   CPC .......... A61M 2205/502; A61M 5/2033; A61M 5/2466; A61M 5/30; A61M 5/3146; A61M 5/31536; A61M 5/31553; A61M 5/31568; A61M 5/31573; A61M 5/31583; A61M 5/31585; A61M 5/36
   USPC ....................................................... 604/201
   See application file for complete search history.

(56) References Cited

FOREIGN PATENT DOCUMENTS

| | | |
|---|---|---|
| WO | 2011/060786 A1 | 5/2011 |
| WO | 2011054755 A1 | 5/2011 |

\* cited by examiner

DRUG DELIVERY DEVICE WITH MOVABLE NEEDLE MOUNT

CROSS-REFERENCE TO RELATED APPLICATIONS

This application is a 35 U.S.C. § 371 National Stage application of International Application PCT/EP2014/074336 (published as WO 2015/071289), filed Nov. 12, 2014, which claims priority to European Patent Application 13192550.5, filed Nov. 12, 2013; this application claims priority under 35 U.S.C. § 119 to U.S. Provisional Application 61/904,277; filed Nov. 14, 2013.

FIELD OF THE INVENTION

The present invention relates to drug delivery devices having means for limiting air entry into the drug reservoir.

BACKGROUND OF THE INVENTION

It is paramount for drug delivery devices to possess the ability to dose accurately in order to ensure that a user receives the intended treatment. Injection devices which comprise a cartridge filled with a medicament and closed with a movable piston, and a dose delivery mechanism including a piston rod for moving the piston are dependent on a precise transfer of the movement of the piston rod to the piston in order to achieve the required dosing accuracy. Any flexibility in a dosing system will affect the dosing accuracy because flexibility will introduce a delay between the movement of the dose delivery mechanism and the piston. If the delay is too large there is a risk that the user will end the injection procedure (e.g. remove the injection needle from the skin) before the intended dose is actually received.

An important contributor to flexibility in the dosing system is the potential presence of air in the medicament. An air bubble in the cartridge will act as a spring and introduce a significant delay to the system. The larger the air bubble the larger the delay that is introduced.

A common misuse of injection devices consists in the user not removing the needle from the needle holding part of the injection unit after an injection. If the needle is not removed air can enter the cartridge through the needle lumen and introduce an uncontrolled delay to the dosing system, thereby compromising the dosing accuracy of the injection device. In order to mitigate this situation users are recommended to prime the device, i.e. to perform an air shot, prior to each injection in order to remove excess air from the cartridge. However, priming is considered a hassle and is sometimes neglected. The usability of injection devices would therefore be significantly improved if the need for air shots could be eliminated.

One way of avoiding air entry into the cartridge through an attached needle is to ensure that fluid communication between the needle and the cartridge is interrupted immediately after an injection. In WO 2011/051366 (Sanofi-Aventis Deutschland GmbH) this is done by retracting the cartridge in the cartridge holder as soon as a dose dispensing procedure has terminated, whereby the needle is pulled out of the cartridge septum. However, by this action the cartridge is displaced relative to the drug delivery device housing, which holds the drive mechanism. The next dose dispensing procedure requires the drive mechanism to firstly displace the cartridge back into fluid communication with the needle before the cartridge piston can be moved to actually dispense a dose. In a precision delivery device the movement of the piston actuator must be closely correlated with the movement of the piston relative to the drug container wall to ensure that the correct dose is expelled. For such delivery devices it is preferable that all advancing movements of the piston actuator are converted directly to advancements of the piston in the drug container because dose delivery is based on a well-defined displacement of the piston actuator relative to the housing. It would be undesirable to additionally take account of a part of the piston actuator movement being used to advance the drug container itself.

SUMMARY OF THE INVENTION

It is an object of the invention to eliminate or reduce at least one drawback of the prior art, or to provide a useful alternative to prior art solutions.

In particular, it is an object of the invention to provide a drug delivery device intended for use with a hollow piercing element, where the possibility of air entering into the drug container due to the piercing element not being removed from the drug delivery device between two consecutive dose expelling procedures is eliminated, or at least significantly reduced.

It is a further object of the invention to provide a drug delivery device of the above kind having a high dosing accuracy and a high dosing reliability.

It is an even further object of the invention to provide a drug delivery device which is easy to handle, which has a simple and intuitive functionality, and which is inexpensive to produce.

In the disclosure of the present invention, aspects and embodiments will be described which will address one or more of the above objects and/or which will address objects apparent from the following text.

In one aspect of the invention a drug delivery device is provided comprising:
  a housing extending along a longitudinal axis,
  a drug reservoir comprising a variable volume chamber and a penetrable self-sealing septum, the drug reservoir being axially fixed with respect to the housing, and
  a needle holder for receiving and holding a fluid delivery structure comprising a back needle portion for penetrating the self-sealing septum, the needle holder being moveable relative to the drug reservoir and the housing between a first position in which a received fluid delivery structure is fluidly disconnected from the variable volume chamber and a second position in which the received fluid delivery structure is fluidly connected with the variable volume chamber.

This provides a construction where the back needle portion can be removed from the chamber regardless of whether the whole fluid delivery structure is removed from the needle holder, notably while the relative axial position of the reservoir and the housing remains the same.

The drug delivery device inherently comprises a dose expelling mechanism, e.g. accommodated at least partially in the housing. The dose expelling mechanism may comprise an actuator activatable to reduce the volume of the variable volume chamber. An activated actuator performs a dose expelling motion relative to the housing. This motion may be purely axial, purely rotational, or both axial and rotational, such as e.g. helical. Since the reservoir is axially fixed with respect to the housing it is possible to ensure that all movements of the actuator affect the volume of the variable volume chamber, whereby a high precision dose delivery can be provided.

The dose expelling mechanism may be partially or fully powered by an energy providing structure, such as e.g. a spring, capable of both releasing and re-storing energy or containing a sufficient amount of energy pre-stored to empty the drug reservoir in one or more energy bursts. The spring may e.g. be a compression spring or a torque spring, or capable of functioning as both a compression spring and a torque spring.

In particular, the dose expelling mechanism may be all mechanical, the omission of electronic dose control components reducing the manufacturing costs and thereby making the dose expelling mechanism attractive for use in a disposable drug delivery device product. An all mechanical dose expelling mechanism does not, however, rule out the possibility of the drug delivery device having an electronic display for indicating e.g. set doses and/or delivered doses, and/or for indicating other dose related information stored in an appurtenant memory. Certain electronic displays can be manufactured very inexpensively by use of state of the art technology.

The reservoir may be axially fixed with respect to the housing via a dedicated reservoir holder. The reservoir holder may be adapted to receive and hold the reservoir and to be releasably or non-releasably attached to the housing, e.g. as is known from the so-called pen injectors. This may be attractive in some cases, e.g. where a glass reservoir is used, because a holder of e.g. plastic can then be provided for easy and stable coupling to the housing. The reservoir holder may alternatively form part of the housing and may be adapted to receive and retain e.g. an end portion of the reservoir.

The needle holder may be inseparably coupled with the drug reservoir and/or with the reservoir holder. In that connection, the first position may be a first predetermined position, e.g. defined by a point of interaction between engaging structures on respectively the needle holder and the drug reservoir or the reservoir holder, and the second position may be a second predetermined position, e.g. defined by a distal portion of the needle holder abutting the drug reservoir or the reservoir holder. This will ensure that the needle holder is not inadvertently removed from the drug delivery device, e.g. during retraction of the back needle portion from the variable volume chamber.

The needle holder may be biased towards the first position such that unless the bias is overcome by a larger force, e.g. from the drug delivery device being pushed towards the skin of a user, the drug delivery device is in a disconnected state where the fluid delivery structure is fluidly disconnected from the chamber. This will provide for an automatic removal of the back needle portion from the chamber in response to the drug delivery device being moved away from a drug delivery site following a dose delivery. The bias may for example be provided by a compression spring acting between the housing, or an element axially fixed with respect to the housing, and the needle holder, or between the drug reservoir, or the reservoir holder, and the needle holder.

In certain embodiments of the invention the needle holder is biased towards the first position by a resilient portion of the needle holder itself. In other embodiments the needle holder is biased towards the first position by a resilient portion of the reservoir holder. In either case, the resilient portion may be a portion of the particular object which is formed as a compression spring. Both the needle holder and the reservoir holder may be made of a polymer, such as e.g. a plastic, and the formation of an integrated spring on either of them will reduce the number of components required to produce the above described effect.

The fluid delivery structure may further comprise a front needle portion for insertion into a skin area of a person. The front needle portion and the back needle portion may be portions of one and the same needle or of different needle structures. In particular, the fluid delivery structure may be a so-called pen needle assembly comprising a needle hub holding a double pointed hollow needle. In accordance therewith, the drug delivery device may be configured for e.g. intradermal, subcutaneous, and/or intramuscular dose administration. Alternatively, the fluid delivery structure may further comprise a nozzle interface for abutment with a skin surface of a person, where the nozzle interface and the back needle portion are fluidly connected. In accordance therewith, the drug delivery device may be configured for high pressure dose administration by jet action.

The drug delivery device may further comprise a dose activation button operable to cause an activation of the actuator. The dose activation button may be axially depressible in the housing to activate the actuator, or to cause energy to be released from an energy providing structure. Further, the needle holder may be axially movable relative to the drug reservoir and the housing between the first position and the second position, and the fluid delivery structure may be configured for insertion into the person by an axial needle insertion movement of the drug delivery device relative to the skin. In that case a dose delivery procedure will involve only a one-dimensional handling of the drug delivery device, which is very simple and convenient for the user to carry out because no change of hand position is required between needle insertion into and needle retraction from the skin.

The drug delivery device may further comprise a dose setting mechanism operable to set a dose to be delivered from the drug reservoir, e.g. as known conventionally in the art of pen injectors.

A mountable and dismountable protective cap may be provided for covering a distal portion of the drug delivery device, such as e.g. a portion of the drug reservoir and/or a portion of the needle holder and/or the fluid delivery structure, when the drug delivery device is in a non-use, or passive, state.

A use of a drug delivery device as described in the above may include either a placement of the nozzle interface on a desired skin location or an insertion of the front needle portion into a particular area of the person's body followed by a penetration of the septum by the back needle portion. In case a user inadvertently activates the dose expelling mechanism while the drug delivery device is in the passive state, such as e.g. during transportation of the device in a bag or pocket or the like, an excess pressure will build up in the chamber. This excess pressure will then cause an instantaneous expelling of drug from the drug reservoir the next time the back needle portion is inserted through the septum as a consequence of the needle holder moving to the second position. In particular if the fluid delivery structure comprises a front needle portion and the front needle portion is already in the skin of the user when the septum is penetrated, this can be critical, as it may lead to a severe overdose.

Thus, in another aspect of the invention a drug delivery device is provided comprising:
    a housing extending along a longitudinal axis,
    a drug reservoir comprising a variable volume chamber and a penetrable self-sealing septum, the drug reservoir being axially fixed with respect to the housing,
    a needle holder for receiving and holding a fluid delivery structure comprising a back needle portion for penetrating the self-sealing septum, the needle holder being moveable relative to the drug reservoir between a first position in which a received fluid delivery structure is fluidly disconnected from the variable volume chamber and a second position in which the received fluid delivery structure is fluidly connected with the variable volume chamber, and a dose expelling mechanism comprising an actuator adapted to, when activated, reduce the volume of the variable volume chamber, the dose expelling mechanism being switchable between a locked state in which activation of the actuator is prevented and an unlocked state in which activation of the actuator is enabled, wherein the dose expelling mechanism is operatively coupled with the needle holder and configured to switch from the unlocked state to the locked state in response to the needle holder being moved to the first position, and to switch from the locked state to the unlocked state in response to the needle holder being moved to the second position, and wherein the needle holder is biased towards the first position.

Thereby, it is guaranteed that no pressure can build up in the drug reservoir due to an inadvertent activation of the dose expelling mechanism when the drug delivery device is in the passive state, because it is simply not possible to activate the actuator if the needle holder is not in the second position. The user is thus never in danger of receiving another dose than the one set (or offered by the drug delivery device in case of a fixed dose delivery device) at the time of putting the device in place for an administration.

As disclosed in the above the actuator may be activatable by operation of a dose activation button, such as e.g. a push button, a slide button, or a touch button. When the dose expelling mechanism is in the locked state the injection button or the actuator, or both, may be disabled.

Accordingly, when the dose expelling mechanism is in the locked state the dose activation button may be rendered inoperable by being mechanically locked against movement in a dose activating direction, e.g. along the longitudinal axis. Alternatively, or additionally, the actuator may be rendered immovable by being mechanically locked against movement in a direction which causes a volume reduction of the variable volume chamber.

Thus, in yet another aspect of the invention a drug delivery device is provided comprising:

a housing extending along a longitudinal axis, a drug reservoir comprising a variable volume chamber and a penetrable self-sealing septum, the drug reservoir being axially fixed with respect to the housing, a needle holder for receiving and holding a fluid delivery structure comprising a back needle portion for penetrating the self-sealing septum, the needle holder being moveable relative to the drug reservoir between a first position in which a received fluid delivery structure is fluidly disconnected from the variable volume chamber and a second position in which the received fluid delivery structure is fluidly connected with the variable volume chamber, and a dose expelling mechanism comprising an actuator adapted to, when activated, reduce the volume of the variable volume chamber, the dose expelling mechanism being switchable between a locked state in which the actuator is locked with respect to the housing and an unlocked state in which the actuator is movable relative to the housing, wherein the dose expelling mechanism is operatively coupled with the needle holder and configured to switch from the unlocked state to the locked state in response to the needle holder being moved to the first position, and to switch from the locked state to the unlocked state in response to the needle holder being moved to the second position, and wherein the needle holder is biased towards the first position.

The switching of the dose expelling mechanism between the locked state and the unlocked state may be realised by incorporation of a blocking structure suitable for obstructing movement of one or more parts of the dose expelling mechanism relative to the housing when the needle holder is in the first position, and for allowing movement of these one or more parts relative to the housing when the needle holder is in the second position. Thereby, the blocking structure may be arranged to disable the dose expelling mechanism in response to a movement of the needle holder from the second position to the first position, and to enable the dose expelling mechanism in response to a movement of the needle holder from the first position to the second position.

The blocking structure may e.g. be coupled with the needle holder and configured to rotate relative to the housing in response to an axial movement of the needle holder relative to the drug reservoir.

The dose expelling mechanism may e.g. be configured to cause a reduction of the volume of the variable volume chamber in response to a rotation of the actuator with respect to the housing. The blocking structure may be rotationally locked with respect to the actuator and further rotationally locked with respect to the housing when the needle holder is in the first position and capable of rotation with respect to the housing when the needle holder is in the second position.

The needle holder may be rotationally locked with respect to the housing, and may comprise coupling structures, such as e.g. teeth, configured for releasable engagement with the blocking structure.

The actuator may be configured to advance helically through a nut member in the housing upon activation. The activation may comprise a rotational motion imparted to the actuator by a guide element. In case the drug delivery device is spring powered the dose expelling mechanism may be configured to release energy from the spring in response to an operation of the dose activation button and to use the energy to rotate the guide element.

In particular embodiments of the invention the needle holder comprises an elongated, e.g. generally cylindrical, structure which in both the first position and the second position extends axially from a distal needle receiving portion to an end portion proximally of the drug reservoir. A portion of the needle holder that is positioned proximally of the drug reservoir is provided with an axially extending corrugated surface which is adapted to slidingly engage with, respectively disengage from, a corresponding corrugated surface on the blocking structure. In the first position of the needle holder relative to the drug reservoir the respective corrugated surfaces provide for a rotationally interlocking engagement between the needle holder and the blocking structure, which prevents the blocking structure from undergoing rotational motion with respect to the housing. Even if the dose activation button is operated, e.g. depressed in the housing, the actuator will not be activated because it will be locked against rotation relative to the housing. When the needle holder is moved to the second position, the respective corrugated surfaces slide out of engagement with one another. This enables rotation of the actuator relative to the housing, and an operation of the dose activation button consequently leads to a dose being expelled from the drug reservoir.

In a further aspect of the invention an injection device is provided comprising:
- a housing extending along a longitudinal axis,
- a cartridge holder adapted to be axially and rotationally fixed with respect to the housing during a use of the injection device,
- a cartridge comprising a cartridge wall, a piston, and a penetrable self-sealing septum, together defining a variable volume chamber, the cartridge being axially retained in the cartridge holder,
- a needle holder comprising a needle mount adapted to receive and hold a fluid delivery structure comprising a back needle portion capable of penetrating the self-sealing wall, the needle holder being moveable relative to the cartridge between a first position in which a received fluid delivery structure is fluidly disconnected from the variable volume chamber and a second position in which the received fluid delivery structure is fluidly connected with the variable volume chamber, and
- a dose expelling mechanism comprising a piston rod adapted to, when activated, reduce the volume of the variable volume chamber, the dose expelling mechanism being switchable between a locked state in which activation of the piston rod is prevented and an unlocked state in which activation of the piston rod is enabled, wherein the dose expelling mechanism is operatively coupled with the needle holder and configured to switch from the locked state to the unlocked state in response to the needle holder being moved to the second position.

In an even further aspect of the invention an injection device is provided comprising:
- a cartridge comprising a cartridge wall, a piston and a penetrable self-sealing septum, together defining a variable volume chamber,
- a fluid delivery structure for conveying substance from the variable volume chamber to an injection site, the fluid delivery structure comprising a back needle portion capable of penetrating the self-sealing septum, and
- an injection unit comprising:
  - a housing extending along a longitudinal axis,
  - a cartridge holder for axially fixing the cartridge with respect to the housing,
  - a needle holder comprising a needle mount adapted to receive and hold the fluid delivery structure, the needle holder being moveable relative to the cartridge holder between a first position in which the back needle portion is fluidly disconnected from the variable volume chamber and a second position in which the back needle portion is fluidly connected with the variable volume chamber,
  - a dose expelling mechanism comprising a piston rod activatable to cause a driving force to be applied to the piston, a spring member adapted to provide energy for activation of the piston rod, and a dose activation button operable to cause a release of energy from the spring member, and
  - a blocking structure configured to disable the dose expelling mechanism in response to the needle holder being moved from the second position to the first position, and to enable the dose expelling mechanism in response to the needle holder being moved from the first position to the second position, wherein the needle holder is biased towards the first position.

The injection device may be suitable for delivery of set doses of drug, and may thus further comprise a dose setting mechanism. The dose setting mechanism may comprise a user operable dose setting button, such as e.g. a dose dial, and a dose counter responsive to operation of the dose setting button to indicate the size of the set dose. The dose counter may comprise an all mechanical structure, such as e.g. a scale drum or an odometer, or it may comprise an electronic display being operatively coupled with the dose setting button, e.g. via a sensing device adapted to determine a change of position of one or more parts in the injection unit.

The housing may be at least substantially cylindrical, such as e.g. circular-cylindrical, or conical, in which case the injection device may be of the pen injector type. Further, an injection button may be provided, e.g. at a proximal end portion of the housing.

The cartridge holder may form part of the housing and may be adapted to receive and retain an end portion of the cartridge. Alternatively, the cartridge holder may be a separate part being structured to receive the entire, or substantially the entire, cartridge, and being adapted for axial and rotational fixation to the housing. The cartridge holder may then alone or in co-operation with one or more other parts of the injection unit fix the cartridge axially with respect to the housing.

The needle holder may be rotationally locked to the cartridge holder to thereby provide a purely axial sliding motion of the needle holder relative to the housing.

A blocking structure may be accommodated in the housing and may be adapted to move relative to the housing between a disabled position, in which a movement of the injection button relative to the housing is prevented, and an enabled position in which a movement of the injection button relative to the housing is allowed.

Further, the needle holder and the blocking structure may be operatively coupled and configured to move the blocking structure from the disabled position to the enabled position in response to the needle holder being moved from the first position to the second position and to move the blocking structure from the enabled position to the disabled position in response to the needle holder being moved from the second position to the first position. Thus, the position of the blocking structure will depend on the position of the needle holder relative to the cartridge, whereby it is ensured that only when the back needle portion has penetrated the septum and established fluid connection to the chamber the dose expelling mechanism can be activated to cause a dose to be delivered. When the back needle is removed from the septum the dose expelling mechanism will be rendered inoperable.

The blocking structure may be rotatably arranged in the housing. In particular, it may be configured to rotate about the longitudinal axis in response to a movement of the needle holder between the first position and the second position.

In the disabled position the blocking structure may take up a first angular position relative to the housing, and in the enabled position the blocking structure may take up a second angular position relative to the housing. The blocking structure may comprise a wall structure of varying radial dimension, and the wall structure may prevent distal movement of the injection button when the blocking structure is in the first angular position relative to the housing and allow distal movement of the injection button when the blocking structure is in the second angular position relative to the housing.

The needle holder may comprise an axially extending structure capable of accommodating at least a portion of the cartridge holder. A proximal portion of the axially extending structure may comprise a segment of a helical groove, and the blocking structure may comprise a protrusion for reception in the groove. A helix angle of the helical groove may be chosen such that an axial movement of the needle holder relative to the housing will cause the protrusion to slide within the helical groove and thereby rotate the blocking structure. This will provide an automatic movement of the blocking structure between the disabled position and the enabled position in response to a movement of the needle holder between the first position and the second position.

Alternatively, the blocking structure may be operatively coupled with the piston rod and arranged to be immobilised in the housing when the needle holder is in the first position and to be free to move relative to the housing when the needle holder is in the second position.

In particular, a proximal portion of the needle holder may be configured to engage with a portion of the blocking structure in response to the needle holder being moved to the first position to thereby fix the blocking structure rotationally with respect to the housing, and to disengage from the portion of the blocking structure in response to the needle holder being moved to the second position. If the blocking structure is rotationally fixed with respect to the piston rod, this will ensure that the piston rod is only capable of rotating relative to the housing when the needle holder is in the second position, i.e. when fluid communication is established between the fluid delivery structure and the variable volume chamber.

Hence, the blocking structure may either passively disable, respectively enable, the dose expelling mechanism, or be activated to disable, respectively enable, the dose expelling mechanism.

In an even further aspect of the invention an injection unit as described in the above is provided, i.e. an injection structure is provided which with the addition of a separate cartridge and a separate fluid delivery structure allows a user to perform injection therapy without risking air entry into the cartridge between injections or premature pressurisation of the variable volume chamber in the cartridge.

Accordingly, an injection unit for an injection device may be provided, where the injection unit comprises a housing extending along a longitudinal axis, a cartridge holder configured to axially fix a drug cartridge with respect to the housing, a needle holder comprising a needle mount adapted to receive and hold a fluid delivery structure comprising a needle structure, a dose expelling mechanism for pressurising an axially fixed drug cartridge, and a blocking structure for selective enabling and disabling of the dose expelling mechanism. The needle holder is movable relative to the cartridge holder between a first position and a second position, where movement from the first position to the second position is converging, and movement from the second position to the first position is diverging, and the needle holder is biased towards the first position. The blocking structure is configured to disable the dose expelling mechanism in response to the needle holder moving from the second position to the first position, and to enable the dose expelling mechanism in response to the needle holder moving from the first position to the second position.

It is noted that in the present context the term "proximal" refers to a portion, position or direction opposite, respectively away from, the outlet end of the drug delivery device, whereas "distal", conversely, refers to a portion, position or direction close to, respectively towards, the outlet end of the drug delivery device.

In the present specification, reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in, or inherent of, at least that one aspect or embodiment of the invention, but not necessarily in/of all aspects or embodiments of the invention. It is emphasized, however, that any combination of the various features, structures and/or characteristics described in relation to the invention is encompassed by the invention unless expressly stated herein or clearly contradicted by context.

The use of any and all examples, or exemplary language (e.g., such as, etc.), in the text is intended to merely illuminate the invention and does not pose a limitation on the scope of the same, unless otherwise claimed. Further, no language or wording in the specification should be construed as indicating any non-claimed element as essential to the practice of the invention.

BRIEF DESCRIPTION OF THE DRAWINGS

In the following the invention will be further described with references to the drawings, wherein.

In the figures like structures are mainly identified by like reference numerals.

DESCRIPTION OF EXEMPLARY EMBODIMENTS

When in the following relative expressions, such as "upwards" and "downwards", are used, these refer to the appended figures and not necessarily to an actual situation of use. The shown figures are schematic representations for which reason the configuration of the different structures as well as their relative dimensions are intended to serve illustrative purposes only.

Figure 1:
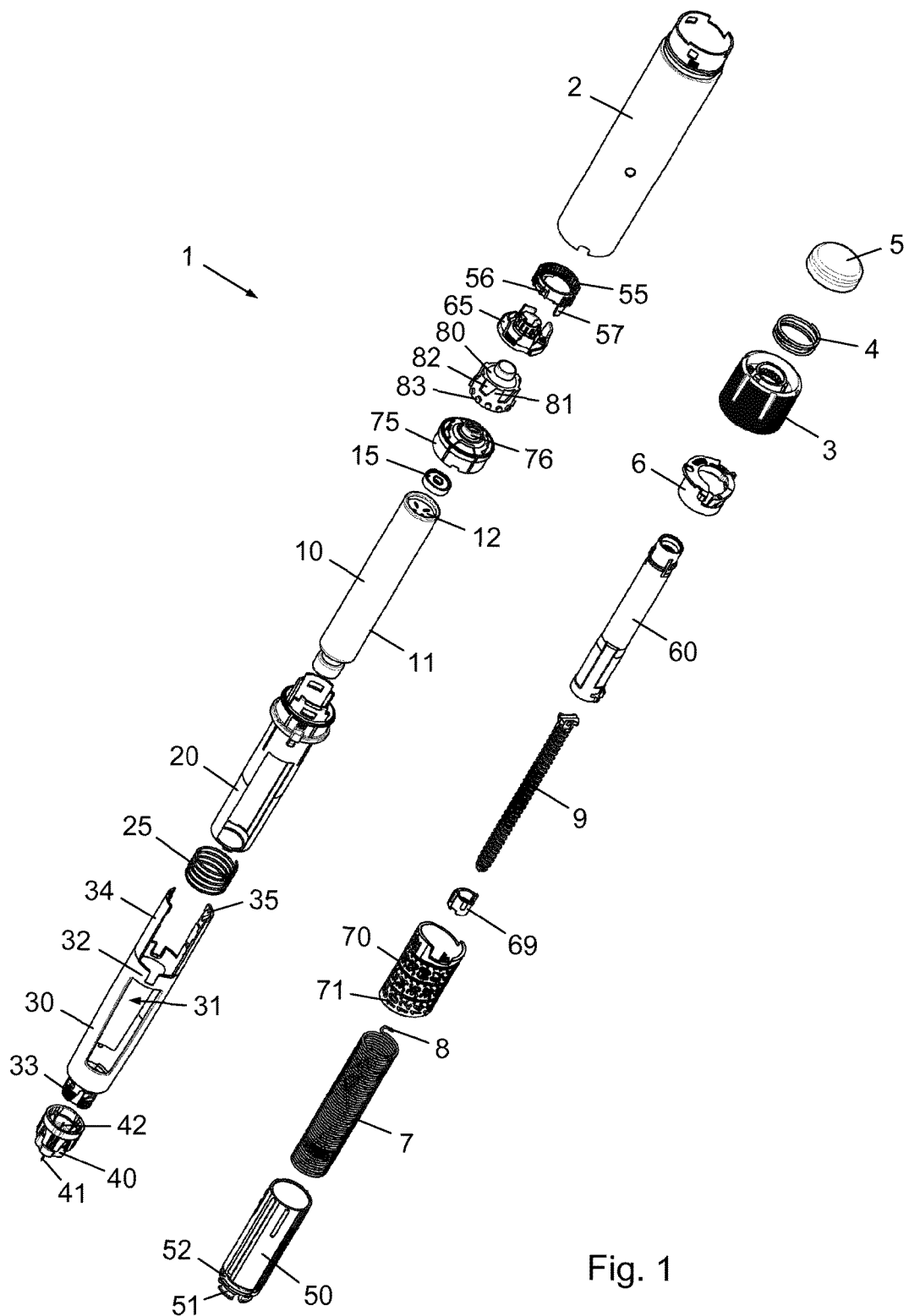
FIG. 1 is an exploded view of a drug delivery device according to a first embodiment of the invention.

FIG. 1 is an exploded view of a drug delivery device according to a first embodiment of the invention. The drug delivery device is an injection device 1 having the general shape of a fountain pen. The injection device 1 comprises an exterior housing 2 extending along a longitudinal axis and a cartridge holder 20 which in use is axially and rotationally locked to the housing 2. The cartridge holder 20 is adapted to receive and hold a cartridge 10 such that the cartridge 10 is at least axially fixed with respect to the housing 2. The cartridge 10 accommodates a slidable piston 12 and is sealed at a drug outlet end by a penetrable self-sealing septum 13

Figures 2, 3:
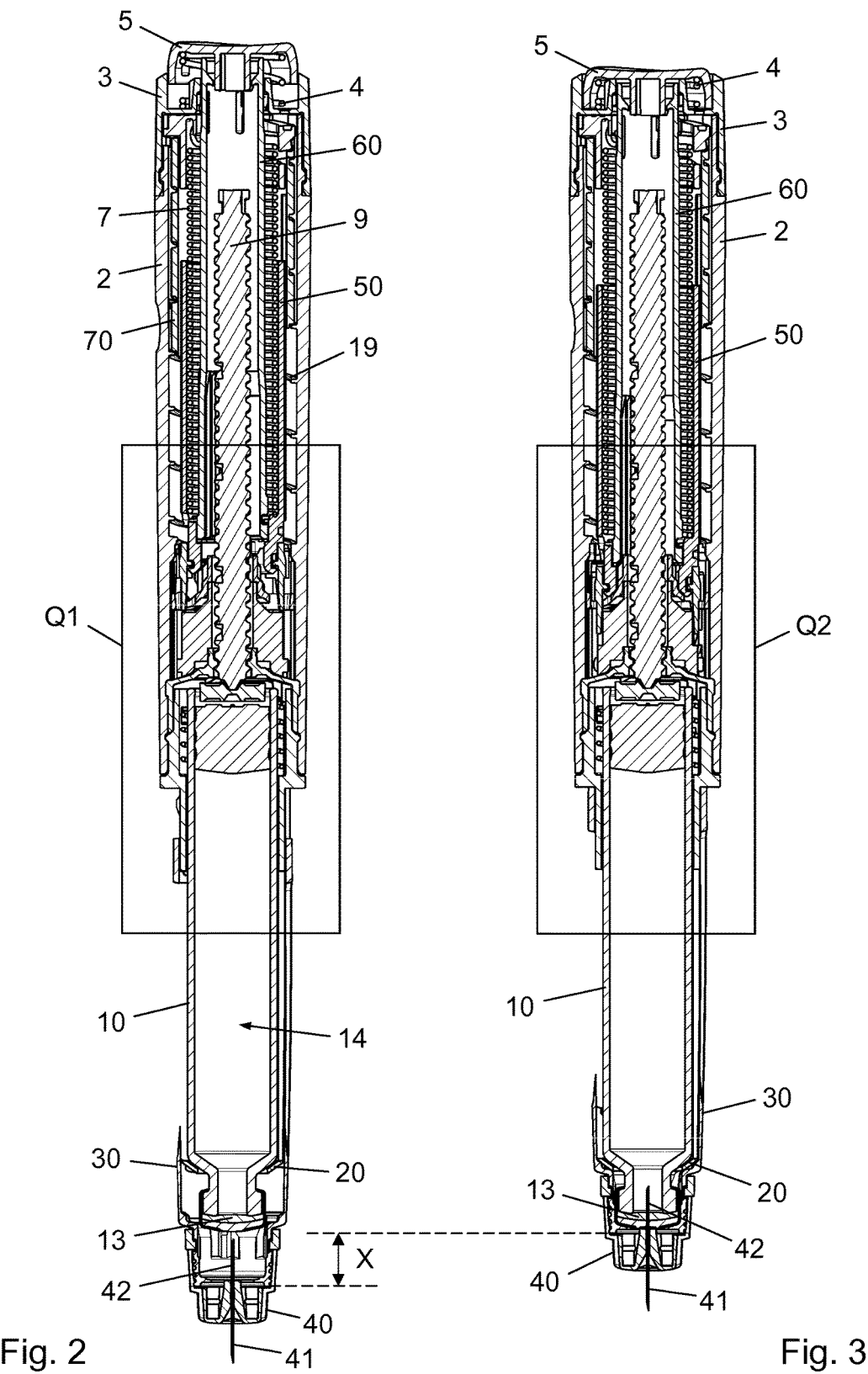
FIG. 2 is a longitudinal section view of the drug delivery device in a pre-use disconnected state.
FIG. 3 is a longitudinal section view of the drug delivery device after establishment of fluid connection between the needle and the reservoir.

(see FIG. 2). The piston 12, the septum 13 and an axially extending cartridge wall 11 together define a variable volume chamber 14 (see FIG. 2) which holds a liquid drug.

A needle carrier 30 comprises a distal needle mount 33 for receiving a needle assembly which includes an injection needle with a front needle portion 41 for insertion into subcutaneous tissue of a person. The needle mount 33 is provided with an external thread and/or bayonet tracks or other means for reception of a needle hub 40 carrying the injection needle. The needle carrier 30 has a generally cylindrical hollow structure with a space 31 for accommodation of the cartridge holder 20 and a circumferential support 32 for proper alignment with the cartridge holder 20. A couple of legs 34 extend proximally from the support 32. Each leg 34 has a helical track segment 35 on a radially inwardly oriented surface. The needle carrier 30 is axially movable relative to the cartridge holder 20, and thereby also relative to the cartridge 10, between a disconnected position, in which an attached needle hub 40 is at such a distance from the cartridge 10 that a back needle portion 42 of the injection needle is spaced apart from the septum 13, and a connected position, in which the needle hub 40 and the cartridge 10 are so close that the back needle portion 42 has penetrated the septum 13 and resides in the chamber 14. A compression spring 25 is arranged to act between the needle carrier 30 and the cartridge holder 20 to bias the needle carrier 30 axially towards the disconnected position.

The piston 12 is displaceable in the cartridge 10 by means of a piston rod 9 acting on a piston washer 15 which is in contact with a portion of the proximal end surface of the piston 12. The piston rod 9 is rotationally engaged with a threaded sleeve 76 of a nut 75 which is axially and rotationally fixed in the housing 2. As will be described further below, the piston rod 9 is movable downwards (distally) through the threaded sleeve 76 by release of a torsion spring 7 arranged to act between a spring base 6, fixedly accommodated in the housing 2, and a driver 50. The driver 50 is axially and rotationally locked to a tube 60, which is again axially locked to an injection button 5 capable of reciprocating axial motion with respect to the housing 2. Hence, all axial movements of the injection button 5 are transferred to the tube 60 and the driver 50. The injection button 5 is arranged in a dose dial 3 and is biased upwards (proximally) by a spring 4.

The torsion spring 7 has a proximal end portion 8 which is retained by the spring base 6 and a distal end portion (not visible) which is received in a spring hold 52. Catch arms 51 are circumferentially distributed at the distal end of the driver 50 and serve to axially fix a clutch 55 to the driver 50. Thereby, the driver 50 and the clutch 55 are translationally locked which means that all axial movements of the driver 50 are transferred to the clutch 55. The driver 50 is rotationally coupled with the clutch 55 via a ratchet mechanism which allows rotation of the driver 50 relative to the clutch 55 in one direction but prevents rotation of the driver 50 relative to the clutch 55 in the opposite direction. The clutch 55 is adapted to move axially between a proximal position in which it is rotationally locked to the housing 2 and a distal position in which it is free to rotate with respect to the housing 2. Axially extending protrusions 56 are provided on the exterior surface of the clutch 55 for rotational locking engagement with mating structures (not visible) in the housing 2 when the clutch 55 is in the proximal position. Further, a couple of fingers 57 extend distally through a piston rod guide 65 which is adapted to transfer movements to the piston rod 9.

A lock member 80 is included and arranged just proximally of the nut 75. The lock member 80 is axially locked with respect to the housing 2, but is capable of rotating about the longitudinal axis between a disabled position, in which respective regular wall portions 81 block distal movement of the respective fingers 57, and an enabled position, in which the respective fingers 57 are allowed to slide along respective indented wall portions 82. The lock member 80 is rotatable via an interaction between respective protrusions 83 on its circumference and the helical track segments 35 in a manner which will be described in more detail below.

The dose dial 3 is operable to set a dose to be delivered from the injection device 1 and is operatively coupled with a scale drum 70 which has a plurality of dose indicia 71 printed on, embossed on, or otherwise applied to its peripheral surface to indicate through a window (not visible) in the housing 2 the size of the dose set as a result of the operation of the dose dial 3. The scale drum 70 is in engagement with a helical rib 19 (see FIG. 2) formed on an inner wall portion of the housing 2.

An end-of-content nut 69 is arranged on the piston rod 9 and serves to prevent a user of the injection device 1 from setting a dose which is larger than the quantum of drug present in the cartridge 10.

A removable cap (not shown) is adapted to be mounted on the injection device 1 to protect the cartridge 10 and to cover the drug outlet end when the injection device 1 is not in use.

FIG. 2 is a longitudinal section view of the injection device 1 in a pre-use state, where the needle carrier 30 is in the disconnected position, i.e. where the back needle portion 42 is spaced apart from the septum 13 and the front needle portion 41 thus is fluidly disconnected from the chamber 14. The scale drum 70 is in its top position in the housing 2 which corresponds to the zero dose position in which no dose is set. The dose dial 3 is rotationally locked to the tube 60, and the scale drum 70 is splined to the driver 50, which means that when the dose dial 3 is turned to set a dose the tube 60, the driver 50 and the scale drum 70 rotate together, further straining the torsion spring 7. Due to the engagement between the scale drum 70 and the rib 19, such rotation will cause the scale drum 70 to travel helically in the housing 2, whereby the dose indicia 71 will sequentially pass by the window.

Regardless of whether a dose is set so long as the needle carrier 30 is in the disconnected position the injection button 5 is inoperable, whereby there is no risk of unintentional activation of the dose delivery mechanism. This will be clear from the below description of FIGS. 4a and 4b.

FIG. 3 is a longitudinal section view of the injection device 1, showing the needle carrier 30 in the connected position, where the needle hub 40 has been moved proximally a distance X to allow the back needle portion 42 to penetrate the septum 13 and enter the chamber 14. In this state of the injection device 1 the injection button 5 is depressible towards the housing 2 against the biasing force of the spring 4, which will be described in more detail below with reference to FIGS. 5a and 5b. In FIG. 3 no dose has been set before the depression of the injection button 5, so even though the dose delivery mechanism in principle has been activated no volume of drug will consequently be delivered from the cartridge 10. However, if a dose had been set the depression of the injection button 5 would have led to the expelling of the set dose through the front needle portion 41.

Figure 4A:
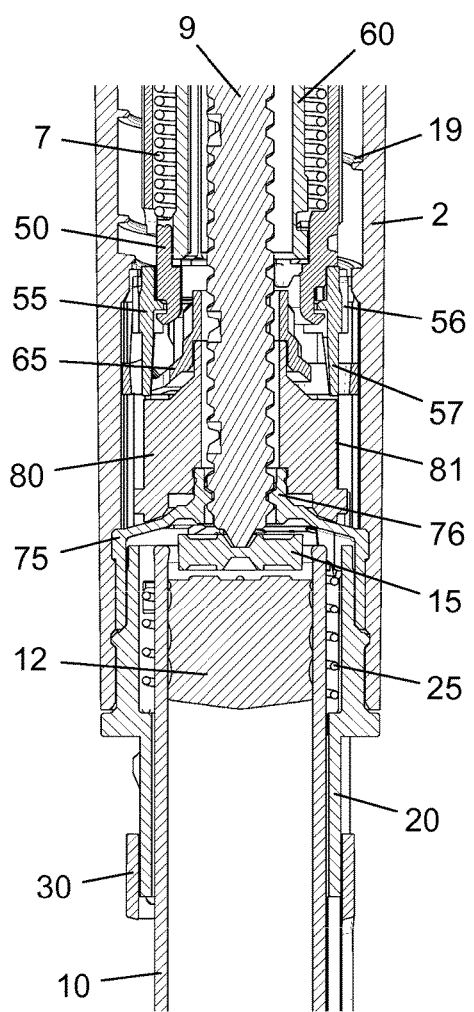
FIG. 4a is an enlargement of the area Q1 in FIG. 2.
Figure 4B:
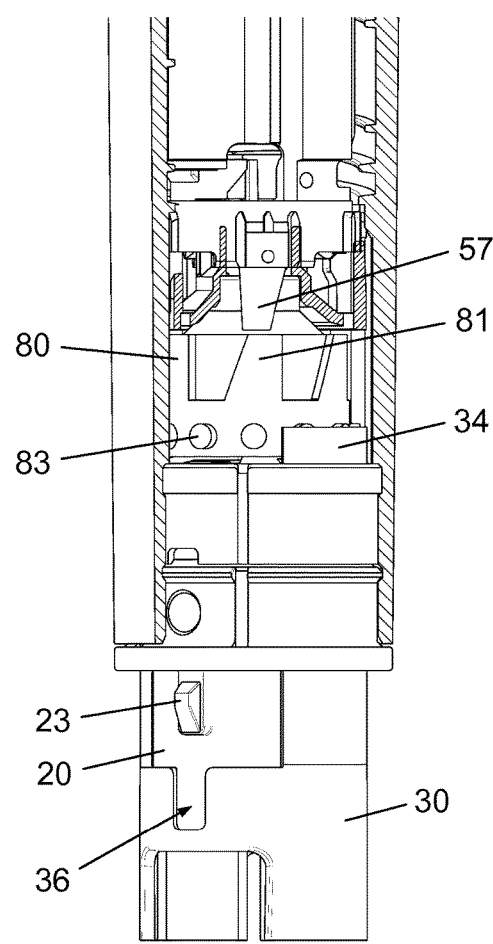
FIG. 4b is a partial section view corresponding to the view of FIG. 4a, FIG. 5a is an enlargement of the area Q2 in FIG. 3.

FIG. 4a is a close-up section view of the portion of the injection device 1 which is indicated by the area Q1 in FIG. 2, and FIG. 4b is a partial section view, partial side view of the same portion. Both figures show the lock member 80 in function. The needle carrier 30 is in the disconnected position which means that each leg 34 is in a distal most position relative to the lock member 80, where respective protrusions 83 are located in upper most positions in the respective helical track segments 35 (FIG. 4b). In this position of the needle carrier 30 the lock member 80 takes up an angular orientation in the housing 2 in which the regular wall portions 81 are aligned with the respective fingers 57 and prevent downward movement of the clutch 55. Since the clutch 55 is axially locked to the injection button 5 via the driver 50 and the tube 60 this orientation of the lock member 80 also prevents downward movement of the injection button 5, i.e. it is not possible to activate the dose delivery mechanism.

FIG. 4b also shows a protrusion 23 on the outer surface of the cartridge holder 20 which is axially spaced apart from a notch 36 in the needle carrier 30, indicating the disconnected position of the latter. The protrusion 23 and the notch 36 are spaced apart a distance corresponding to the distance X.

Figure 5A:
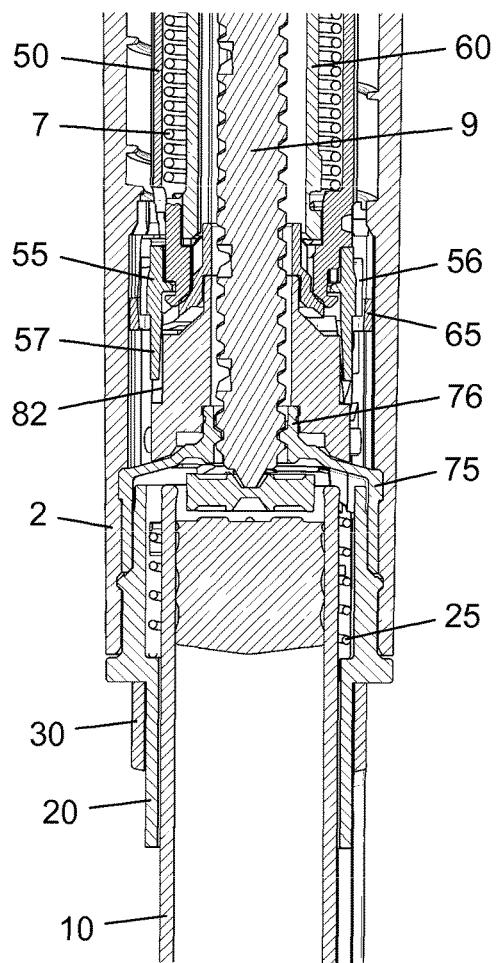
FIG. 5b is a partial section view corresponding to the view of FIG. 5a, and FIGS. 6 and 7 are section views of a portion of a drug delivery device according to a second embodiment of the invention.
Figure 5B:
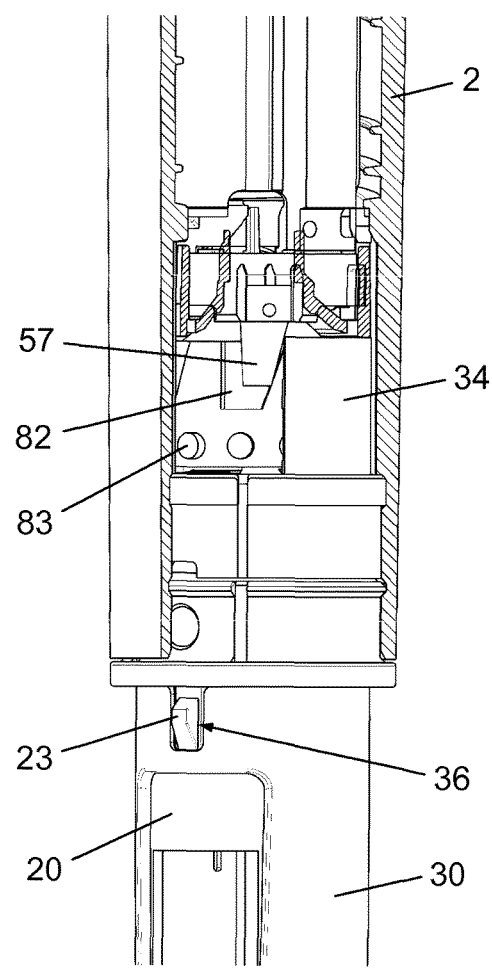

FIG. 5a is a close-up section view of the portion of the injection device 1 which is indicated by the area Q2 in FIG. 3, and FIG. 5b is a partial section view, partial side view of the same portion. The needle carrier 30 has moved proximally and non-rotationally along the cartridge holder 20 and is now in the connected position in which the protrusion 23 is received in the notch 36 (FIG. 5b). This corresponds to the case where a user has inserted the front needle portion 41 into the skin by forcing the injection device 1 towards a desired injection site. Notably, the needle carrier 30 is designed to undergo the proximal movement simultaneously with or subsequent to the insertion of the front needle portion 41 to avoid any accidental activation of the dose delivery mechanism before the injection needle is properly positioned in the user.

During the proximal movement of the needle carrier 30 each leg 34 has forced a protrusion 83 to travel downward in its helical track segment 35, whereby the lock member 80 has been rotated with respect to the housing 2 so as to take up a new angular orientation in which the indented wall portions 82 are aligned with the respective fingers 57. This allows the clutch 55 to move distally in the housing 2, with the fingers 57 sliding along the indented wall portions 82, when the injection button 5 is subjected to a push force from a user, and the injection device 1 is thus ready to deliver a set dose.

Due to the axial relationship between the injection button 5, the tube 60, the driver 50, and the clutch 55 when the injection button 5 is depressed the clutch 55 is moved to the distal position, and when the injection button 5 is returned by the spring 4 the clutch 55 is moved to the proximal position. The interface between the scale drum 70 and the spring base 6 together with the interface between the scale drum 70 and the driver 50, the ratchet mechanism coupling the driver 50 and the clutch 55, and the rotational lock of the clutch 55 in the proximal position enable a rotational pre-stressing of the torsion spring 7 during assembly of the injection device 1.

In the distal position the clutch 55 engages rotationally with the piston rod guide 65 which is rotationally locked with respect to the piston rod 9. As mentioned above the piston rod 9 is engaged by the threaded sleeve 76 of the stationary nut 75. Hence, a rotation of the clutch 55 will lead to a rotation of the piston rod guide 65 and through that to a rotation of the piston rod 9. The threaded sleeve 76 converts the rotation of the piston rod 9 to a helical motion, whereby the piston rod 9 is displaced axially with respect to the cartridge 10.

To set a dose to be delivered from the cartridge 10 the dose dial 3 is turned clockwise (seen from the proximal end of the injection device 1) a number of degrees until the scale drum 70 shows the desired dose through the window in the housing 2. This will result in a similar clockwise rotation of the tube 60 and, through the above described rotational relationship, also of the driver 50. When the injection button 5 is not depressed the clutch 55 is in its proximal position in which it is prevented from rotating with respect to the housing 2. The driver 50 therefore rotates clockwise with respect to the clutch 55. This rotation of the driver 50 will twist the torsion spring 7 between the driver 50 and the stationary spring base 6. Due to the ratchet interface between the driver 50 and the clutch 55 the torsion spring 7 will not be able to return to its original state during the dose dialing, so the driver 50 will remain rotationally biased until the injection button 5 is depressed.

When the injection button 5 is depressed against the bias of the spring 4 the clutch 55 will, as described above, move to the distal position. During this shift the clutch 55 rotationally engages with the piston rod guide 65 and further moves out of engagement with the housing 2, thereby releasing the torsion spring 7. The torque from the torsion spring 7 then causes the driver 50, the clutch 55, and the piston rod guide 65 to rotate counter-clockwise, whereby the piston rod 9 rotates counter-clockwise and, due to the threaded interface with the nut 75, advances the piston 12 in the cartridge 10 to expel the drug through the injection needle. Further, the release of the torsion spring 7 returns the scale drum 70 to the zero dose position along the helical rib 19 in the housing 2. Since the scale drum 70 and the driver 50 are rotationally interlocked the zero dose position defines the maximum extent of counter-clockwise rotation of the driver 50.

Since the injection button 5 is biased proximally by the spring 4 when the push force is terminated the clutch 55 is automatically moved back to its proximal starting position. Further, since the needle carrier 30 is biased towards the disconnected position by the compression spring 25 a removal of the front needle portion 41 from the skin of the user causes the needle carrier 30 to automatically move distally relative to the cartridge holder 20 until mutually mating protrusions (not visible) on the two prevent further distal movement of the needle carrier 30. During this movement the protrusions 83 are forced to travel upward in the respective helical track segments 35, causing the lock member 80 to rotate back to the original angular orientation in which the regular wall portions 81 are aligned with the respective fingers 57. Thus, when the injection needle is removed from the user the back needle portion 42 is automatically retracted from the septum, and the injection button 5 is automatically locked against depression into the housing 2, thereby preventing activation of the dose delivery mechanism.

Notably, in case the user withdraws the injection needle from the skin during a dose expelling procedure no excessive pressure will be built up in the cartridge 10. Either the injection needle is withdrawn while the injection button 5 is depressed, in which case the drug will simply keep flowing out of the injection needle because an interaction between the fingers 57 and the regular wall portions 81 (as depicted in FIG. 5b) will prevent a rotation of the lock member 80 towards the original angular orientation relative to the housing 2, thereby preventing the biasing force from the compression spring 25 from moving the needle carrier 30 towards the disconnected position, or the injection needle is withdrawn after release of the injection button 5, in which case the bias of the spring 4 on the injection button 5 has caused a movement of the clutch 55 to its proximal position, thereby retaining the torsion spring 7.

Figure 6:
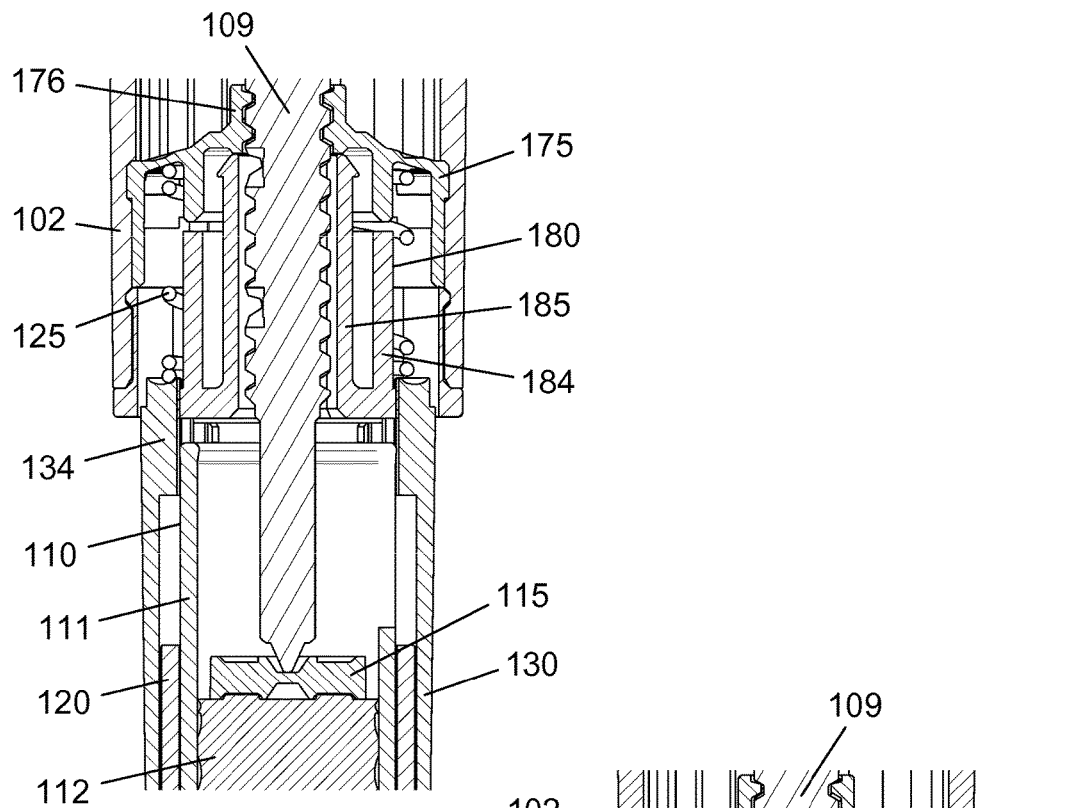

FIG. 6 is a close-up section view of a portion of an injection device according to a second embodiment of the invention. With the exception of the lock feature this injection device is structurally and functionally similar to the injection device 1 described above in connection with the first embodiment of the invention, i.e. the respective dose setting mechanisms and dose delivery mechanisms, as well as the relative movements between the needle carrier and the cartridge holder, are identical.

The figure shows a portion of the injection device which corresponds largely to the portion of the injection device 1 delimited by the area Q1. Specifically, the injection device comprises a needle carrier 130 which is arranged slidably relative to a cartridge holder 120 supporting a cartridge 110 that is sealed by a piston 112. A piston rod 109 adapted to cause movement of the piston 112 via a piston washer 115 is engaged with a threaded sleeve 176 of a nut 175 arranged stationarily in a housing 102. The needle carrier 130 is biased distally by a compression spring 125 arranged to act between the nut 175 and a pair of toothed proximal end portions 134, which in the shown distal, or disconnected, position of the needle carrier 130 are in rotational locking engagement with a circumferential band of teeth 181 (visible in FIG. 7) provided on a lock member 180.

The lock member 180 comprises an outer cylindrical wall 184 and an inner cylindrical wall 185. The inner cylindrical wall 185 has axial splines which engage with axial grooves (not visible) in the piston rod 109 to provide for a rotational interlocking connection between the lock member 180 and the piston rod 109.

The needle carrier 130 is rotationally locked with respect to the cartridge holder 120 and the housing 102, so in the state of the injection device shown in FIG. 6 the lock member 180 is prevented from undergoing any rotation relative to the housing 102. This means that the piston rod 109 is prevented from rotating in the threaded sleeve 176, and thereby from advancing downwards to displace the piston 112.

Hence, whereas the lock member 80 incorporated in the injection device 1 prevents the injection button 5 from being depressed against the housing 2 the lock member 180 prevents the piston rod 109 from rotating in the housing 102. The injection button (not shown) associated with the injection device according to the second embodiment of the invention is thus depressible against the housing 102 at all times, but when the needle carrier 130 is in the disconnected position the interaction between the toothed proximal end portions 134 and the teeth 181 prevent the torsion spring (not shown) from releasing energy because the piston rod 109 is rotationally fixed in the housing 102 via the lock member 180.

Figure 7:
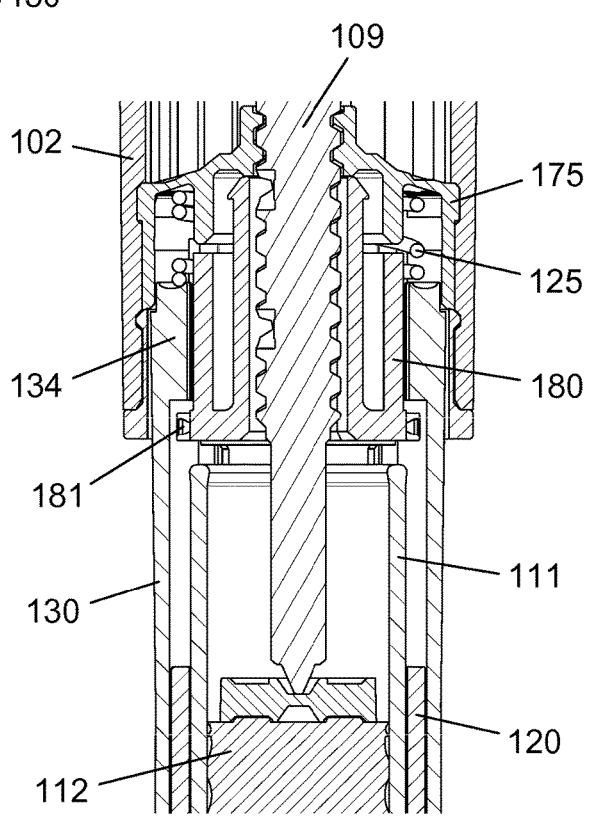

In FIG. 7 the needle carrier 130 has been moved to the connected position, i.e. to its proximal most position relative to the housing 102 and the cartridge holder 120. This reflects a situation where a user has exerted an axial force to a distal end of a needle hub (not visible) attached to the needle carrier 130 in the course of inserting an injection needle (not visible) into the skin.

The displacement of the needle carrier 130 relative to the housing 102 has caused the toothed proximal end portions 134 to move axially relative to the outer cylindrical wall 184 and thereby disengage from the teeth 181. Thus, in this relative position of the needle carrier 130 and the cartridge holder 120 the lock member 180 is allowed to rotate with respect to the housing 102, which means that a depression of the injection button will cause the dose delivery mechanism to expel a set dose from the cartridge 110 in a manner similar to what is described above in connection with the first embodiment of the invention.

In case the user withdraws the injection needle from the skin during a dose expelling procedure no excessive pressure will be built up in the cartridge 110, because once the compression spring 125 forces the needle carrier 130 towards the disconnected position the toothed proximal end portions 134 move back into rotational locking engagement with the teeth 181, thereby preventing rotation of the lock member 180 and the piston rod 109 relative to the housing 102. The torsion spring (not shown) is thus retained and no driving force is applied to the piston 112.

The invention claimed is:

1. An injection unit for an injection device, the injection unit comprising:
    a housing extending along a longitudinal axis,
    a cartridge holder configured to axially fix a drug cartridge with respect to the housing,
    a needle holder comprising a needle mount adapted to receive and hold a fluid delivery structure, the needle holder being moveable relative to the cartridge holder between a first position and a second position, where movement from the first position to the second position is converging, and movement from the second position to the first position is diverging, and where the needle holder is biased towards the first position,
    a dose expelling mechanism for pressurising an axially fixed drug cartridge, the dose expelling mechanism comprising a piston rod, a spring member adapted to provide energy for activation of the piston rod, and a dose activation button operable to cause a release of energy from the spring member, and
    a blocking structure configured to disable the dose expelling mechanism in response to the needle holder being moved from the second position to the first position, and to enable the dose expelling mechanism in response to the needle holder being moved from the first position to the second position, wherein the blocking structure is movable relative to the housing between a disabled position in which movement of the dose activation button relative to the housing is prevented and an enabled position in which movement of the dose activation button relative to the housing is allowed,
    wherein the needle holder and the blocking structure are coupled such that when the needle holder moves from the first position to the second position the blocking structure moves from the disabled position to the enabled position, and when the needle holder moves from the second position to the first position the blocking structure moves from the enabled position to the disabled position.

2. The injection unit according to claim 1, wherein the cartridge holder and the needle holder are inseparable.

3. The injection unit according to claim 1, wherein the needle holder is biased towards the first position by a resilient portion of the needle holder or of the cartridge holder.

4. The injection unit according to claim 1, wherein the blocking structure is axially fixed with respect to the housing and configured to rotate about the longitudinal axis in response to the needle holder moving between the first position and the second position.

5. The injection unit according to claim 4, wherein the needle holder is rotationally fixed with respect to the housing and comprises a proximal extension with a groove defining a helical track segment, and wherein the blocking structure comprises a protrusion slidingly arranged in the groove.

6. The injection unit according to claim 4, wherein the blocking structure comprises a circumferentially corrugated wall structure extending along the longitudinal axis,
wherein distal motion of the dose activation button along the longitudinal axis is prevented by the wall structure at a first angular orientation of the blocking structure relative to the housing which corresponds to the disabled position, and
wherein distal motion of the dose activation button is allowed at a second angular orientation of the blocking structure relative to the housing which corresponds to the enabled position.

7. The injection unit according to claim 6, wherein the dose expelling mechanism further comprises an axially extending tube axially locked to the dose activation button, a drive member axially locked to the tube, and a clutch axially locked to the drive member,
wherein the circumferentially corrugated wall structure comprises regular wall portions and radially indented wall portions, and
wherein in the first angular orientation of the blocking structure at least one regular wall portion abuts the clutch, and in the second angular orientation of the blocking structure the clutch is slidable along the radially indented wall portions.

8. The injection unit according to claim 1, wherein the needle holder is rotationally fixed with respect to the housing,
wherein the blocking structure is rotationally fixed to the piston rod, and
wherein in the first position the needle holder and the blocking structure are rotationally interlocked and in the second position the needle holder and the blocking structure are rotationally decoupled.

9. The injection unit according to claim 8, wherein the blocking structure is axially fixed with respect to the housing, and
wherein the needle holder comprises a first toothed structure, and the blocking structure comprises a second toothed structure configured for interlocking engagement with the first toothed structure in the first position of the needle holder and for axial disengagement from the first toothed structure during movement of the needle holder from the first position to the second position.

10. The injection unit according to claim 9, wherein the dose expelling mechanism further comprises an axially extending tube axially locked to the dose activation button, a drive member axially locked to the tube, and a clutch axially locked to the drive member and axially movable with respect to the housing, by operation of the dose activation button, between an anchored position in which the clutch is rotationally fixed to the housing and a freed position in which the clutch is capable of rotation in the housing under influence of the spring structure, and
wherein in the freed position the clutch is rotationally locked to the piston rod.

11. An injection unit according to claim 1, wherein the dose expelling mechanism is all mechanical.

12. An injection device comprising:
a cartridge comprising a cartridge wall, a piston and a penetrable self-sealing septum, together defining a variable volume chamber,
a fluid delivery structure for conveying substance from the cartridge to an injection site, the fluid delivery structure comprising a back needle portion capable of penetrating the self-sealing septum, and
an injection unit comprising:
a housing extending along a longitudinal axis,
a cartridge holder configured to axially fix a drug cartridge with respect to the housing,
a needle holder comprising a needle mount adapted to receive and hold the fluid delivery structure, the needle holder being moveable relative to the cartridge holder between a first position in which the back needle portion is fluidly disconnected from the variable volume chamber and a second position in which the back needle portion is fluidly connected with the variable volume chamber,
a dose expelling mechanism comprising a piston rod activatable to cause a driving force to be applied to the piston, a spring member adapted to provide energy for activation of the piston rod, and a dose activation button operable to cause a release of energy from the spring member, and
a blocking structure configured to disable the dose expelling mechanism in response to the needle holder being moved from the second position to the first position, and to enable the dose expelling mechanism in response to the needle holder being moved from the first position to the second position;
wherein when the needle holder is biased towards the first position.

13. The injection device according to claim 12, wherein the fluid delivery structure further comprises a front needle portion being fluidly connected with the back needle portion and adapted for insertion into a skin area of a person by a needle insertion movement of the injection device relative to the skin area, and
wherein the movement of the needle holder between the first position and the second position is parallel to the needle insertion movement.

14. The injection device according to claim 13, wherein the movement of the needle holder between the first position and the second position and the needle insertion movement are parallel to the longitudinal axis, and
wherein the spring structure is configured to release energy to activate the piston rod in response to a displacement of the dose activation button relative to the housing along the longitudinal axis.

15. The injection device according to claim 12, wherein the cartridge holder and the needle holder are inseparable.

16. The injection device according to claim 12, wherein the needle holder is biased towards the first position by a resilient portion of the needle holder or of the cartridge holder.

17. The injection device according to claim 12, wherein the blocking structure is movable relative to the housing between a disabled position in which movement of the dose activation button relative to the housing is prevented and an enabled position in which movement of the dose activation button relative to the housing is allowed, and
wherein the needle holder and the blocking structure are coupled such that when the needle holder moves from the first position to the second position the blocking structure moves from the disabled position to the enabled position, and when the needle holder moves from the second position to the first position the blocking structure moves from the enabled position to the disabled position.

18. The injection device according to claim 17, wherein the blocking structure is axially fixed with respect to the housing and configured to rotate about the longitudinal axis in response to the needle holder moving between the first position and the second position.

19. The injection device according to claim 18, wherein the needle holder is rotationally fixed with respect to the housing and comprises a proximal extension with a groove defining a helical track segment, and wherein the blocking structure comprises a protrusion slidingly arranged in the groove.

20. The injection device according to claim 18, wherein the blocking structure comprises a circumferentially corrugated wall structure extending along the longitudinal axis,
wherein distal motion of the dose activation button along the longitudinal axis is prevented by the wall structure at a first angular orientation of the blocking structure relative to the housing which corresponds to the disabled position, and
wherein distal motion of the dose activation button is allowed at a second angular orientation of the blocking structure relative to the housing which corresponds to the enabled position.

21. The injection device according to claim 20, wherein the dose expelling mechanism further comprises an axially extending tube axially locked to the dose activation button, a drive member axially locked to the tube, and a clutch axially locked to the drive member,
wherein the circumferentially corrugated wall structure comprises regular wall portions and radially indented wall portions, and
wherein in the first angular orientation of the blocking structure at least one regular wall portion abuts the clutch, and in the second angular orientation of the blocking structure the clutch is slidable along the radially indented wall portions.

22. The injection device according to claim 12, wherein the needle holder is rotationally fixed with respect to the housing,
wherein the blocking structure is rotationally fixed to the piston rod, and
wherein in the first position the needle holder and the blocking structure are rotationally interlocked and in the second position the needle holder and the blocking structure are rotationally decoupled.

23. The injection device according to claim 22, wherein the blocking structure is axially fixed with respect to the housing, and
wherein the needle holder comprises a first toothed structure, and the blocking structure comprises a second toothed structure configured for interlocking engagement with the first toothed structure in the first position of the needle holder and for axial disengagement from the first toothed structure during movement of the needle holder from the first position to the second position.

24. The injection device according to claim 23, wherein the dose expelling mechanism further comprises an axially extending tube axially locked to the dose activation button, a drive member axially locked to the tube, and a clutch axially locked to the drive member and axially movable with respect to the housing, by operation of the dose activation button, between an anchored position in which the clutch is rotationally fixed to the housing and a freed position in which the clutch is capable of rotation in the housing under influence of the spring structure, and
wherein in the freed position the clutch is rotationally locked to the piston rod.

25. The injection device according to claim 12, wherein the dose expelling mechanism is all mechanical.

* * * * *